United States Patent
Ando et al.

(10) Patent No.: US 10,338,046 B2
(45) Date of Patent: Jul. 2, 2019

(54) ARTIFICIAL OLFACTORY SENSING SYSTEM

(71) Applicant: HITACHI, LTD., Chiyoda-ku, Tokyo (JP)

(72) Inventors: Masahiko Ando, Tokyo (JP); Sanato Nagata, Tokyo (JP); Shirun Ho, Tokyo (JP); Yuji Suwa, Tokyo (JP); Mitsuharu Tai, Tokyo (JP); Kenzo Kurotsuchi, Tokyo (JP); Hiromasa Takahashi, Tokyo (JP); Norifumi Kameshiro, Tokyo (JP); Seiichi Suzuki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/760,777

(22) PCT Filed: Jan. 15, 2016

(86) PCT No.: PCT/JP2016/051063
§ 371 (c)(1),
(2) Date: Mar. 16, 2018

(87) PCT Pub. No.: WO2017/122338
PCT Pub. Date: Jul. 20, 2017

(65) Prior Publication Data
US 2018/0267005 A1   Sep. 20, 2018

(51) Int. Cl.
*C12M 1/34* (2006.01)
*G01N 27/27* (2006.01)
(Continued)

(52) U.S. Cl.
CPC ........... *G01N 33/0031* (2013.01); *C12M 1/34* (2013.01); *G01N 27/4141* (2013.01); *G01N 27/27* (2013.01)

(58) Field of Classification Search
CPC ........... G01N 33/0031; G01N 27/4141; G01N 27/27; C12M 1/34
(Continued)

(56) References Cited

U.S. PATENT DOCUMENTS

2009/0066347 A1* 3/2009 Uenluebayir .......... G01N 27/12
324/686
2010/0147683 A1* 6/2010 Vanaja ............... G01N 33/5438
204/403.01
(Continued)

FOREIGN PATENT DOCUMENTS

JP   2003083932 A   3/2003
JP   2011007741 A   1/2011
(Continued)

OTHER PUBLICATIONS

Nikkei Electronics, "Odors Open New Doors: Revolutions in Healthcare, Logistics and Interpersonal Relationships", Jun. 2015, pp. 59-69 (pp. 59, translated).
(Continued)

*Primary Examiner* — Bo Fan
(74) *Attorney, Agent, or Firm* — Procopio, Cory, Hargreaves & Savitch LLP (57) ABSTRACT

An object of the present invention is to provide an artificial olfactory sensing system capable of sniffing out various odors highly sensitively.
The artificial olfactory sensing system includes: plural sensor cells on a lipid membrane of each of which olfactory receptors have developed; and plural ion-sensitive field-effect transistors (ISFETs) that correspondingly exist to the sensor cells on a one-on-one basis. A response signal showing that each of the olfactory receptors of each of the sensor cells has recognized an odor molecule is converted into an electric signal by an ISFET corresponding to each of the sensor cells.

8 Claims, 7 Drawing Sheets

(51) Int. Cl.
*G01N 33/00* (2006.01)
*G01N 27/414* (2006.01)

(58) Field of Classification Search
USPC .......................... 257/253, 687, 723; 438/113
See application file for complete search history.

(56) References Cited

U.S. PATENT DOCUMENTS

2012/0143027 A1\* 6/2012 Phillips .............. G01N 27/4145
600/345
2015/0247819 A1 9/2015 Shi et al.

FOREIGN PATENT DOCUMENTS

JP 2013027376 A 2/2013
JP 2015503729 A 2/2015

OTHER PUBLICATIONS

H. Mitsuno et al., "Novel cell based odorant sensor elements based on insect odorant receptors," Biosensors and Bioelectronics, pp. 287-294, vol. 65, (2015).
Y. Hirose et al., "Development of Bio-transistor with Olfactory Cell Interface for Cancer Detection," The 75th JSAP Autumn Meeting, Lecture Proceedings (Autumn, 2014, Hokkaido University: Lecture No. 19p-A2-6).
H. Sakano "Neural map function in the mouse olfactory system," Oyo Butsuri 83(1), (2014).
P. Wang et al. "Cell based Biosensors and its Application in Biomedicine," Sensors and Actuators B, (2005) vol. 108, issue 1-2, pp. 576-584.

\* cited by examiner

ARTIFICIAL OLFACTORY SENSING SYSTEM

TECHNICAL FIELD

The present invention relates to an artificial olfactory sensing system which utilizes a combination of biological substances and semiconductor technologies.

BACKGROUND ART

Sensing technologies, which artificially duplicate the five senses and have capabilities superior to the capabilities of organisms, will become indispensable technologies for protecting the safe, healthy, and untroubled living conditions in these diversified human societies and global environments. If an odor sensor (an artificial olfactory sensing system) that is as excellent as the odor sensor of an organism is put into practice, information that has not been used yet becomes usable, so that there is a possibility that such information is applied to robots, self-driving vehicles, medical care, and the like (refer to Nonpatent Literature 1, for example).

It is said that sensors that highly sensitively sense a few specific molecules such as an explosive-derived molecule, so-called specialist-type sensors, will be put into practice in the near future using a technology brought about by fusing biotechnologies and nano-technologies. On the other hand, as for an artificial olfaction system that sniffs out a large number of odor patterns including a mixer of plural kinds of molecules from background odors, that is, a so-called generalist-type artificial olfaction system, although the studies about the relevant biotechnology and semiconductor technology have been started, this generalist-type artificial olfaction system has not been put into practice yet.

As one of biotechnologies, a technology regarding an odor sensor that uses sensor cells each of which includes a biological olfactory receptor made artificially using biotechnology is disclosed (refer to, for example, Nonpatent Literature 2 and Patent Literature 1).

In addition, as one of semiconductor technologies, an achievement in which a response to the volatile odorous substance of the olfactory epithelium cells of a mouse is detected as an electrical signal using an ion-sensitive field-effect transistor is disclosed (refer to, for example, Nonpatent Literature 3).

Furthermore, as a technology brought about by combining a biotechnology with a semiconductor technology, a technology regarding a configuration and a method, by which an optical or an electrical response generated at the time when an olfactory receptor of an olfactory cell extracted from an organism recognizes an odor molecule is measured using a field-effect transistor, is disclosed (refer to, for example, Nonpatent Literature 2).

The technologies disclosed in Patent Literature 1 and Nonpatent Literatures 2 and 3 are olfactory sensing systems specialized for sensing specific molecules, that is, they are so-called specialist-type olfactory sensing systems. To put it concretely, only insect pheromone molecules can be detected by the technologies disclosed in Patent Literature 1 and Nonpatent Literature 2, and only VOCs (volatile organic compounds), which are biomarkers regarding cancers, can be detected by the technology disclosed in Nonpatent Literature 3.

Figure 7:
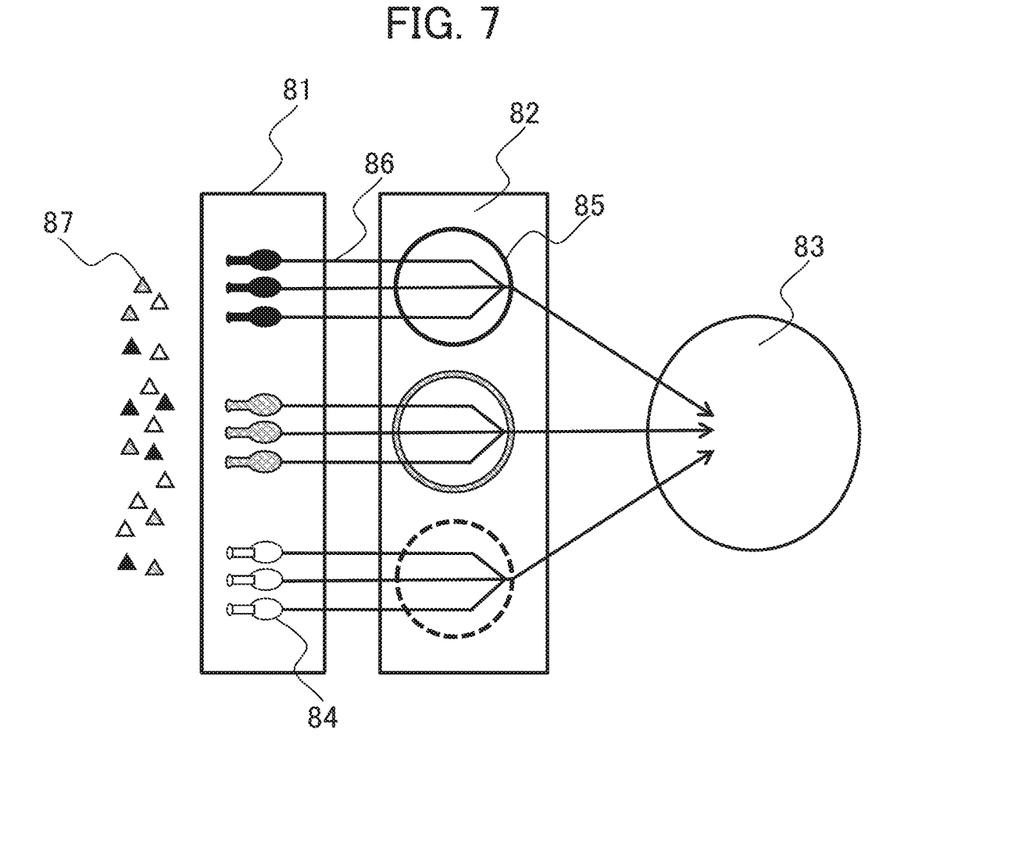
FIG. 7 is a schematic diagram showing the olfactory nerve system of a mammal typified by a human being.

On the other hand, a configuration for realizing a generalist-type artificial olfactory system will be explained with reference to a schematic diagram of the olfactory nerve system of a mammal typified by a human being shown in FIG. 7. When the olfactory nerve system of a mammal is roughly divided, the olfactory nerve system includes three regions, that is, (1) an olfactory epithelium 81, (2) an olfactory bulb 82, and (3) a brain 83.

There are plural kinds of olfactory cells 84 on the olfactory epithelium 81 inside a nasal cavity, and plural olfactory cells 84 of the same kind are neurologically connected to a single corresponding glomerulus 85 on an olfactory bulb 82 via axons 86. There is a loose relationship of a key and a keyhole between an odor molecule 87 and an olfactory cell 84, and signals issued by plural olfactory cells 84 which have recognized odor molecules 87 are added up at the corresponding glomerulus 85, and the firing pattern of the glomerulus 85 corresponding to the relevant odor pattern is displayed on the olfactory bulb 82.

The brain 83 identifies the relevant odor by retrieving odor memories stored in the brain itself and by comparing the retrieved memories with the firing pattern displayed on the olfactory bulb 82. Because the signals of plural olfactory cells 84 are added up at a glomerulus 85, the noises included in the signals cancel each other, so that the S/N ratios of the signals are improved.

A human being has about 400 kinds of olfactory cells 84 on the olfactory epithelium 81, in which each kind of olfactory cells issues a response signal different from response signals issued by other kinds to odor molecules 87 and the number of each kind of olfactory cells is about 1,000. Here the simplest case is considered where each olfactory cell 84 responds to a certain odor molecule 87 by issuing two different responses signals "0" and "1". In this case, because $2^{400}$ ($=2.5 \times 10^{120}$) kinds of response signals different from each other are issued in response to the odor molecule 87, if it becomes possible to associate these odor pattern signals with odor memories, a generalist-type artificial olfactory sensing system can be realized.

In order to build such a generalist-type artificial olfactory sensing system, (1) plural kinds of olfactory cells 84 that recognizes odor molecules 87 and issues different response signals, or odor molecule sensor groups equivalent to the plural kinds of olfactory cells 84, (2) glomeruli 85 each of which adds up response signals of plural olfactory cells of the same kind, or odor signal adding-up mechanisms equivalent to the glomeruli 85, and (3) a brain 83 that compares odor patterns issued by the plural glomeruli 85 or by the plural odor signal adding-up mechanisms with odor memories, or a retrieval algorithm that carries out the function of the brain 83 on the behalf of the brain 83, and a retrieval device including the retrieval algorithm are required.

A technology regarding such a generalist-type sensor is disclosed in Patent Literature 2. In Patent Literature 2, a generalist-type olfactory sensing system is built using olfactory cells and glomeruli derived from an organism.

CITATION LIST

Patent Literature

Patent Literature 1: Japanese Unexamined Patent Application Publication No. 2013-27376
Patent Literature 2: Japanese Unexamined Patent Application Publication No. 2011-7741

Nonpatent Literature

Nonpatent Literature 1: Nikkei Electronics, June 2015, p. 59.

Nonpatent Literature 2: H. Mitsuno et al., "Novel cell based odorant sensor elements based on insect odorant receptors," Biosensors and Bioelectronics 65, pp. 287-294 (2015).

Nonpatent Literature 3: Yuichi Hirose et al., "Development of bio-transistor with olfactory cell interface for cancer," The $75^{th}$ JSAP Autumn Meeting, Lecture Proceedings (Autumn, 2014, Hokkaido University: Lecture Number 19p-A2-6).

Nonpatent Literature 4: Hitoshi Sakano, "Neural map function in the mouse olfactory system," OYO BUTSURI 83(1), p. 18, (2014)

SUMMARY OF INVENTION

Technical Problem

Generally speaking, in a live organism, about 1,000 olfactory cells of the same kind are connected to a common glomerulus, while olfactory cells of other kinds are not connected erroneously to the common glomerulus as described above, and that mechanism has already become apparent (refer to, for example, Nonpatent Literature 4).

Nevertheless, it is practically difficult to bring out a nerve cell network, which three-dimensionally includes glomeruli to which plural olfactory cells are neurologically connected, from an organism in a way disclosed in Patent Literature 2. Alternatively, although a method can be considered in which glomeruli each of which is corresponding to individually-extracted olfactory cells are selectively connected in accordance with a configuration disclosed in Nonpatent Literature 4, it is difficult to realize this configuration in environments other than in a live organism.

As described above, there is a problem in that various odors composed of plural kinds of molecules cannot be sniffed out highly sensitively because, in the related generalist-type artificial olfactory sensing systems, there is no means for selectively connecting plural olfactory cells of the same kind to the same glomerulus or to the same odor adding-up mechanism.

An object of the present invention is to provide an artificial olfactory sensing system capable of sniffing out various odors highly sensitively.

Solution to Problem

In order to realize the above object, the present invention adopts a configuration including plural sensor cells on a lipid membrane of each of which olfactory receptors have developed, and plural ion-sensitive field-effect transistors (ISFETs) that are corresponding to the sensor cells on a one-on-one basis. In addition, in the above configuration, a response signal showing that each of the olfactory receptors of each of the sensor cells has recognized an odor molecule is converted into an electric signal by an ISFET corresponding to each of the sensor cell.

Advantageous Effects of Invention

According to the present invention, it is possible to sniff out various odors highly sensitively.

DESCRIPTION OF EMBODIMENTS

One embodiment according to the present invention will be explained in detail with reference to the accompanying drawings.

First Embodiment

Figure 1:
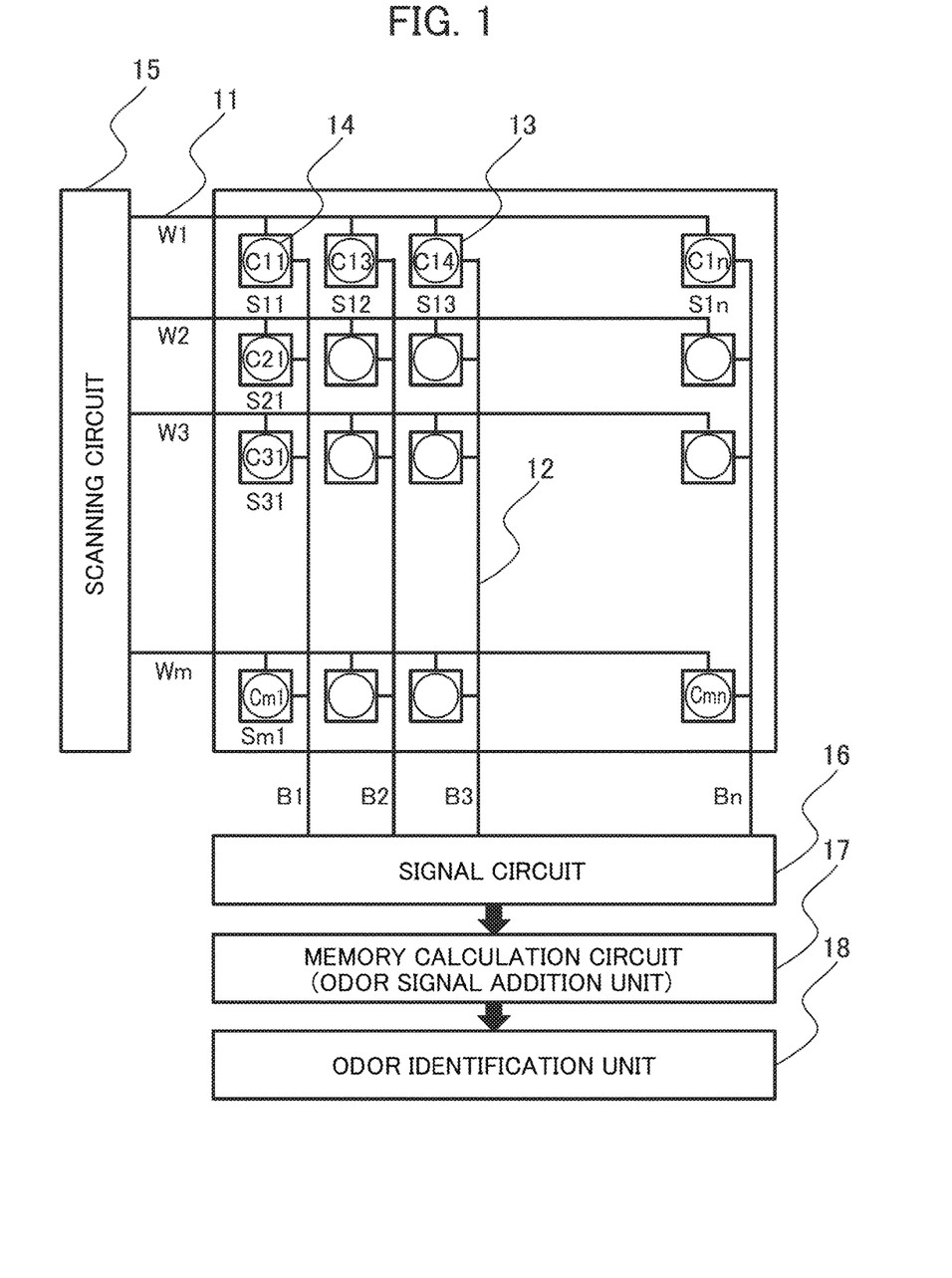
FIG. 1 is a block diagram of an artificial olfactory sensing system that is one embodiment according to the present invention.

FIG. 1 is a block diagram of an artificial olfactory sensing system according to this embodiment. Sensor sections Sij (i=1 . . . m, j=1 . . . n) 13 are disposed at the cross-points of m scanning wirings Wi (i=1 . . . m) 11 and n signal wirings Bj (j=1 . . . n) 12, that is, the sensor sections Sij (i=1 . . . m, j=1 . . . n) 13 are disposed in an m-by-n matrix arrangement, and sensor cells Cij (i=1 . . . m, j=1 . . . n) 14 are disposed on the sensor sections Sij. For example, if m=n=1000, sensor cells Cij are disposed on one million sensor sections Sij on a one-on-one basis. The scanning wires Wi are connected to a scanning circuit 15, and the signal wirings Bj are connected to a signal circuit 16 respectively, and the signal circuit Bj is connected to a memory calculation circuit (an odor signal addition unit) 17, and the memory calculation circuit is connected to an odor identification unit 18.

Figure 2:
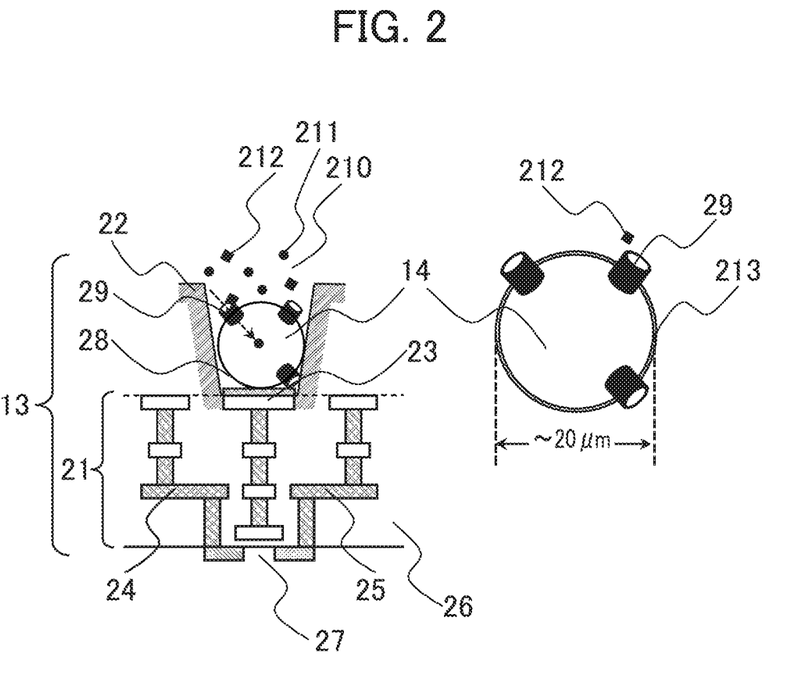
FIG. 2 is an overview cross-sectional diagram for explaining the main components of a sensor section shown in FIG. 1.

FIG. 2 is a cross-sectional diagram showing the detailed configuration of a sensor section 13 and a sensor cell 14 shown in FIG. 1. The sensor section 13 includes an ion-sensitive field-effect transistor (ISFET) 21, and a well 22 disposed on the ISFET, and at least one sensor cell 14 is disposed in the well 22. The ion-sensitive transistor 21 includes: a gate electrode 23; a drain electrode 24; a source electrode 25; an insulating film 26; and a semiconductor 27, and carrier charges are accumulated in the semiconductor 27 that is in contact with the insulating film 26 at the interface between the semiconductor 27 and the insulating film 26 due to a gate voltage applied to the gate electrode 23, so that a current flows according to a voltage applied between the drain electrode 24 and the source electrode 25.

The sensor cell 14 is in contact with the gate electrode 23 via a contact electrode 28 that is made of a noble metal such as gold or platinum, or made of alloyed metal including gold or platinum as needed. The sensor cell 14 is provided mainly with the olfactory receptors 29 of an insect, and is soaked in a physiological aqueous solution 210 with its pH adjusted. Ca ions 211 and odor molecules 212 are distributed in the physiological aqueous solution 210, and when an olfactory receptor 29 recognizes an odor molecule 212, the ion channel of the olfactory receptor 29 is opened and Ca ions flow into the sensor cell 14, so that the potential of the surface of the sensor cell 14 changes.

This potential change is transmitted to the gate electrode 23, carrier charges are accumulated at the interface between the insulating film 26 and the semiconductor 27, and a current flows between the drain electrode 24 and the source electrode 25, so that a response signal showing that the olfactory receptor 29 recognizes the odor molecule 212 is converted into an electric signal. As the sensor cell 14, a sensor cell disclosed in Patent Literature 1 or Patent Literature 2 can be used.

As a host cell, any cell can be used without limitation as long as it is a *Spodoptera frugiperda*-derived cell, and for example, an Sf21 cell, an Sf9 cell, or the like is preferable. Among the above cells, the Sf21 cell can live under a wide temperature range 18° C. to 40° C., and the Sf21 cell does not need carbon dioxide for adjusting the PH of a culture solution used for the Sf21, so that it is especially preferable that the Sf21 cell can be used semipermanently. By selecting sensor cells 14 the diameters of which are role 20 μm out of sensor cells that are made of the above host cell using a porous filter, it becomes possible to dispose at least one sensor cell 14 in the well 22 the diameter of which is about 20 μm.

The inside and the outside of the sensor cell 14 are separated from each other by the lipid membrane 213, and a Ca concentration in the inside of the sensor cell 14 is kept lower than that in the outside of the sensor cell by the actions of ion pumps that have developed on the surface of the lipid membrane 213. On the other hand, when an olfactory receptor 29, which has developed on the lipid membrane 213 as is the case of the ion pumps, recognizes an odor molecule 212, the ion channel of the olfactory receptor 29 is opened and Ca ions 211 flow from the outside of the sensor cell 14 into the inside. As a result, the potential change of the lipid membrane 213 of the sensor cell 14 is transmitted to the gate electrode 23 via the contact electrode 28, and the ISFET 21 becomes in an on-state. The magnitude of this on-state is converted into an electric signal.

Figure 3:
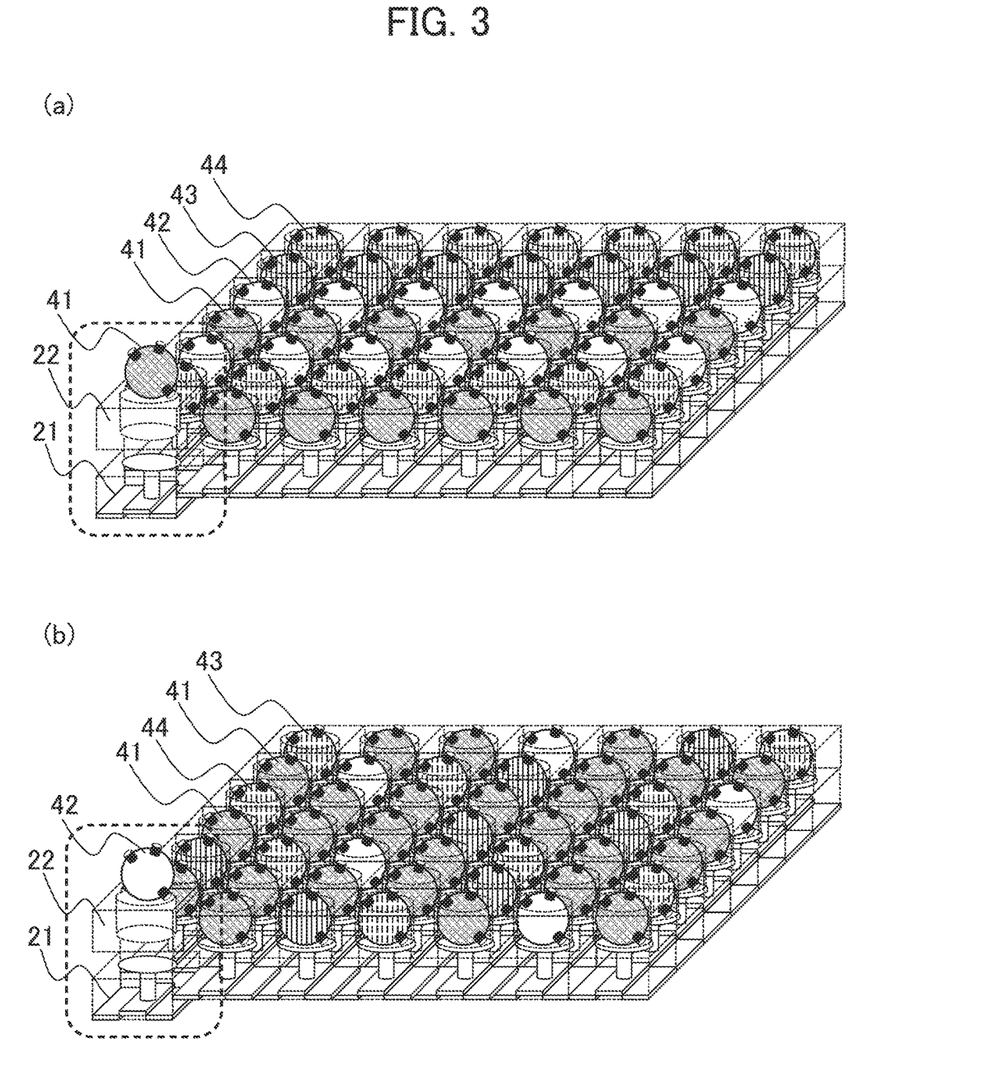
FIG. 3 is a schematic view showing an example of an arrangement in which plural sensor cells are disposed on an ISFET two-dimensional matrix array.

FIG. 3 is a schematic view showing an arrangement in which plural kinds of sensor cells (four kinds of sensor cells in this example) are disposed on an ISFET two-dimensional matrix array.

FIG. 3(*a*) shows a configuration in which four kinds of sensor cells 41 to 44 are disposed in wells 22 each of which is formed on an ISFET 21 and exposes a contact electrode 28 (refer to FIG. 1) covering the gate electrode of the ISFET 21 on its bottom, and this configuration is characterized in that sensor cells of the same kind are disposed on ISFETs 21 connected to a common scanning wiring (refer to FIG. 1).

In this case, because a selection voltage is simultaneously applied to selection transistors connected to a common scanning wirings, and the selection transistors are turned on, output signals (or current pulse widths) that are generated at sensor cells disposed on the common scanning wirings are received by the signal circuit 16 (refer to FIG. 1) and then added up by the memory calculation circuit 17, so that the output signals of the sensor cells of the same kind can be added up in the relevant scanning cycle. As for output signals output from sensor cells of the same kind disposed on different scanning wirings, it is conceivable that these signals are respectively memorized by the memory calculation circuit 17, and then they are added up.

As described above, if sensor cells of the same kind are disposed on a common scanning wiring, there is an advantageous effect that the output signals of these sensor signals can be added up simultaneously. In order to dispose different kinds of sensor cells at desired positions on the two-dimensional matrix ISFET array respectively, a micropipette and a microscope are required, and it is possible to dispose one million (=1,000×1,000) sensor cells by using an automated sensor cell alignment device.

FIG. 3(*b*) shows a configuration in which four kinds of sensor cells 41 to 44 are disposed in wells 22 each of which is formed on an ISFET 21 and exposes a contact electrode 28 (refer to FIG. 1) covering the gate electrode of the ISFET 21 on its bottom, and this configuration is characterized in that different kinds of sensor cells are randomly disposed on ISFETs 21 connected to a common scanning wiring. Therefore, in order to add up output signals output from sensor cells of the same kind, it is necessary that output signals output in a time series from sensor cells by line-sequential scanning driving should be temporarily stored in the memory calculation circuit, and after scanning during the relevant scanning cycle is over, only the signal outputs from the sensor cells of the same kind should be selectively added up.

In the disposition of the sensor cells shown FIG. 3(*a*), because the dispositions of the respective sensor cells are predetermined, if the dispositions are accurately carried out, it is not necessary to check the dispositions of the respective sensor cells after the disposition. On the other hand, because the dispositions of the different kinds of sensor cells shown in FIG. 3(*b*) are random, after the dispositions are executed, it is necessary to measure and store the kinds and the dispositions of the sensor cells for the following addition processing. A method for performing the following processing will be explained with reference to FIG. 4.

Figure 4:
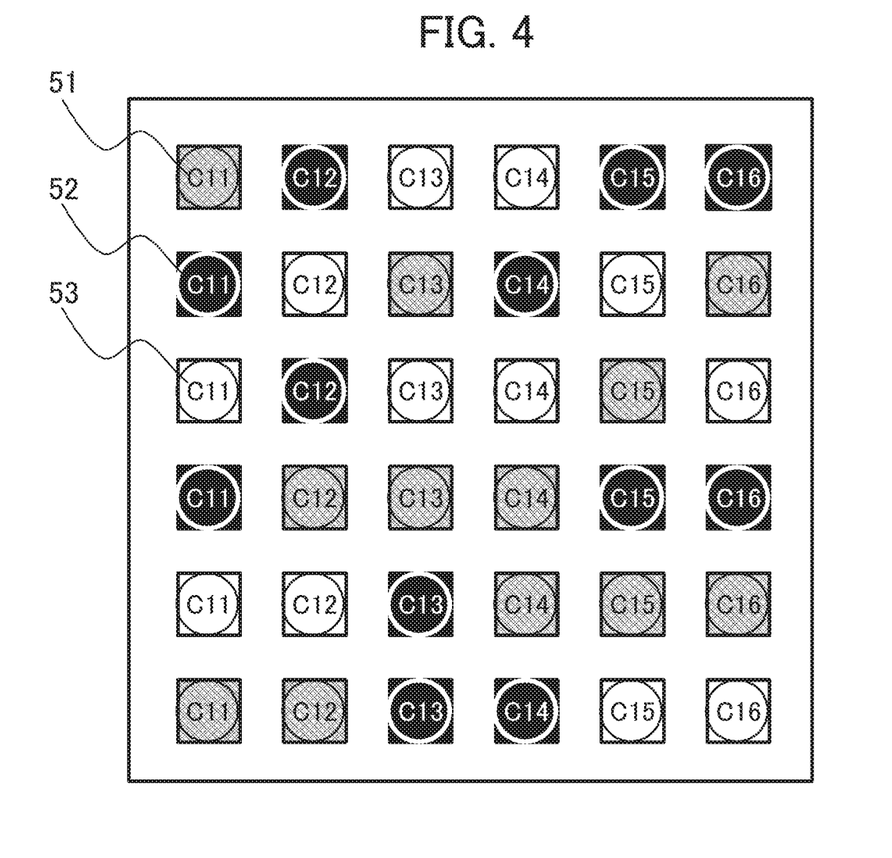
FIG. 4 is a schematic view showing three kinds of sensor cells disposed on a 6-by-6 ISFET two-dimensional matrix array.

FIG. 4 is a schematic view showing three kinds of sensor cells A51, B52, and C53 that are randomly disposed on a 6-by-6 two-dimensional matrix ISFET array. Sensor cells of each kind respectively include olfactory receptors that are different from those of sensor cells of the other two kinds, and the former olfactory receptors identify and respond to especially intensely an odor molecule group that is different from odor molecule groups that are identified and responded to especially intensely by the sensor cells of the other two kinds. Here the above three odor groups are referred to as a, b, and c. It will be assumed that the odor molecule group a is responded to especially intensely by the sensor cells A 51 and is responded to not so intensely by the sensor cells B 52 and C 53, so that the odor molecule group a can be identified. The odor molecule groups b and c can be selected using the sensor cells B52 and C53 respectively in a similar way. The locations of the sensor cells A 51, B 52, and C 53 are specified using the odor molecule groups a, b, and c provided in such a way through the following steps.

First, the artificial olfactory sensing system is run for a certain time using only the odor molecule group a. In the case where the system is run for plural cycles and the output signals of each sensor section are added up, the added-up value of the output signals of each sensor section in which a sensor cell A is disposed shows an expressly greater value than that of each sensor section in which a sensor cell B or a sensor cell C is disposed after the system is run for three or four cycles though this number of cycles varies according to the odor molecular concentration. In this way, the locations of the sensor cells A can be specified. The locations of the sensor cells B and C can also be specified by similar steps using the odor molecule groups b and c respectively.

If the locations of various kinds of sensor cells are specified in advance, when a typical odor molecule measurement is performed, the output signals of sensor cells of the same kind can be added up. Nevertheless, it sometimes happens that the intensities of output signals obtained by adding up the output signals of sensor cells of the same kind in response to odor molecule groups having the same concentrations are different from each other. For this reason, it is necessary to normalize the intensities of the output signals in response to the stimuli of odor groups having the same concentrations.

Figure 5:
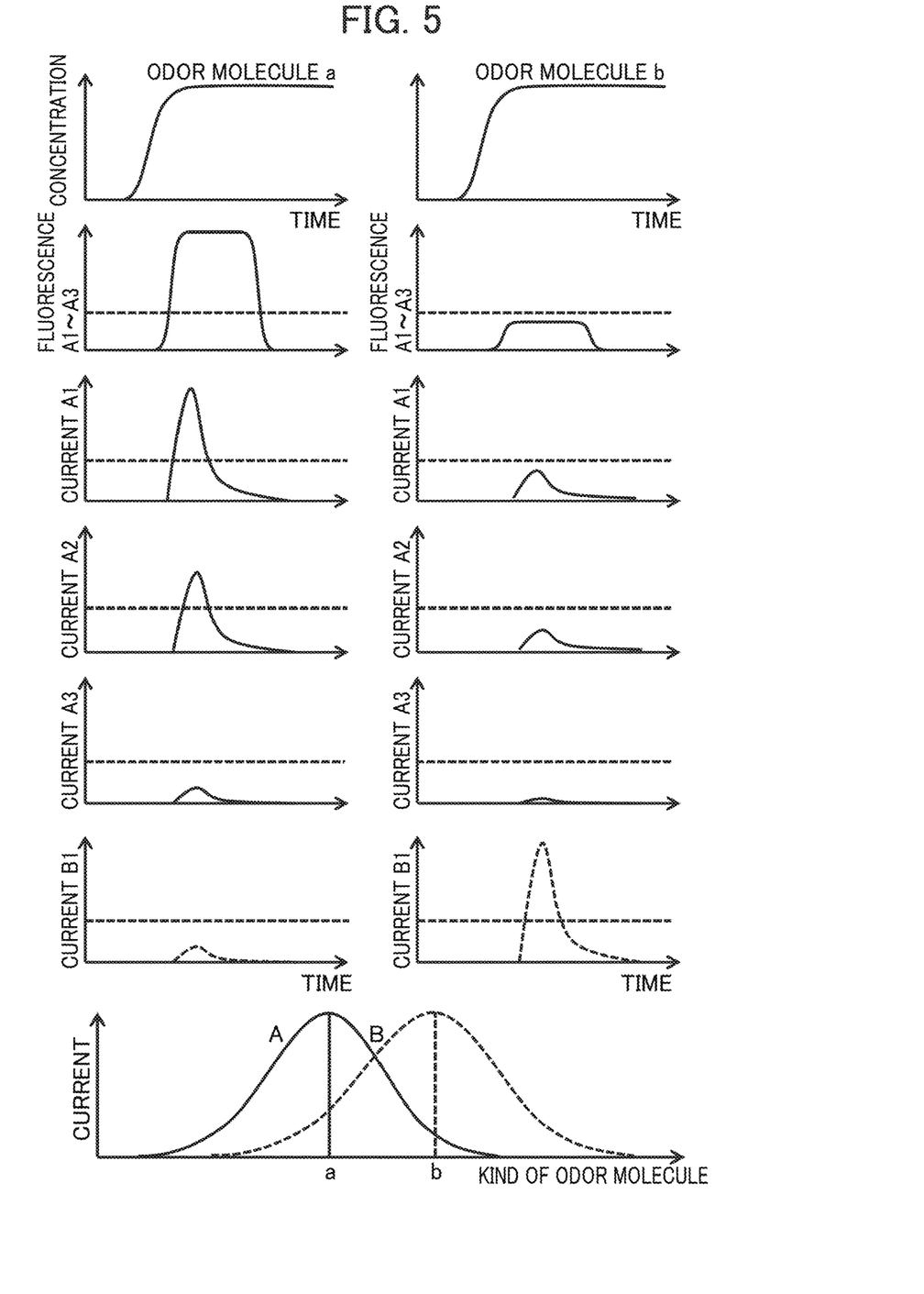
FIG. 5 is a diagram showing the time changes of the optical responses and the electric responses of two kinds of sensor cells in response to odor stimuli.

FIG. 5 shows the time changes of the optical responses and the electric responses of two kinds of sensor cells A and B the sensitivities of which are respectively high in response to the stimuli of two kinds of odor molecule groups a and b.

In the sensor cell A, there are three kinds of sensor cells A1, A2, and A3 that have respectively different intensities of response currents in response to the stimulus of the same odor molecule. Furthermore, as is clear from the strong dependency of the intensities of the response currents of the sensor cells A and B on the kinds of odor molecules shown in a graph in the lowest row of FIG. 5, the sensor cells A and B have sensitivities to the odor molecules b and a respectively although the sensitivities are very low while the sensor cells A and B show the greatest reaction currents to the odor molecules a and b respectively. Therefore, it cannot be judged simply that sensor cells that respond to the odor molecule a and the odor molecule b are a sensor cell A and a sensor cell B respectively.

The normalization method and the selection method of the intensities of the signals of sensor cells will be explained with reference to FIG. 5. First, the fluorescent responses of the sensor cells A1, A2, and A3 in response to the stimuli of the odor molecules a and b shown in graphs in the highest row in FIG. 5 are almost the same as shown in graphs in the second row from the top in FIG. 5. Judging from the above, it will be understood that the sensor cells A1 to A3 are sensor cells that show the same responses to the same odor stimulus.

On the other hand, if the sensor cells A1, A2, and A3 show fluorescent responses having different intensities respectively to the same odor stimulus, it will be interpreted in such a way that there are variations among the performances of the sensor cells of the same kind. Causes for these variations are considered to be the numbers of olfactory receptors developing on the lipid membranes of the sensor cells being different from each other, the positions of the sensor cells relative to the openings of the relevant wells being different from each other, the numbers of Ca ion responsive proteins developing in the sensor cells being different from each other, and the like.

As shown in graphs in the third to fifth rows from the top in FIG. 5, it was observed that there were differences among the intensities of electric signal conversions, which were performed via ISFETs and detection circuits, in the sensor cells A1, A2, and A3 that show the same optical responses. The above differences are assumed to be due to the differences among the characteristics of the electric contacts between the sensor cells and the contact electrodes on the gate electrodes of the ISFETs of the sensor cells, where the differences among the characteristics are considered to be generated due to the variations of the shapes of the sensor cells and the variations of the locations of the well.

Both intensities of the response currents of the sensor cells A1 and A2 are larger than thresholds shown in dashed lines respectively (refer to the left graphs in the third and fourth row from the top in FIG. 5). In this case, after all the response currents of the sensor cell A are normalized, all these response currents are added up by the memory calculation circuit. After these normalization factors are extracted by a protocol used for specifying the locations of the respective sensor cells shown in FIG. 4 and stored in the memory calculation circuit in advance, the response signals of the respective sensor cells are multiplied by the relevant normalization factors respectively in an actual odor measurement, and cumulative addition is carried out on the multiplied response signals.

On the other hand, in the case of the sensor cell A3, the intensity of the response current of the sensor cell A3 does not reach a threshold (refer to a left graph in the fifth row from the top in FIG. 5), therefore it is difficult to distinguish the intensity of the response current of the sensor cell A3 from the intensity of the response current of the sensor cell B in response to the odor molecule a. In addition, variations due to disturbances caused by external signal noises are also large. For this reason, because the signal of the sensor cell A3 is not added up to the actual cumulative addition for the odor identification, a normalization factor is set to 0.

By adopting the above protocol, it becomes possible to correct the variations of the intensities of signals associated with the electric signal conversion that are generated due to the variations of the locations of sensor cells for the stimuli of odor molecules having the same concentration on a sensor section array of a two-dimensional matrix arrangement, and the response characteristics of generalist-type sensor cells, which respond to non-mainstream odor molecules as shown in the lowest row of FIG. 5, are quantitatively converted into electric signals, and obtained electric signals are cumulatively added up, which makes it possible to build an artificial olfactory sensing system that is capable of distinguishing a large number of odor patterns using plural generalist-type sensor cells just like an organism.

An artificial olfactory sensing system, in which the response signals of sensor cells are converted into electric signals and addition processing are performed on the electric signals, has a feature that retrieving time and energy can be cut down by limiting the number of kinds of sensor cells used for retrieving to a minimum necessary number in accordance with the type of an odor molecule group to be retrieved and any organism does not have this feature. This feature will be explained with reference to FIG. 6.

Figure 6:
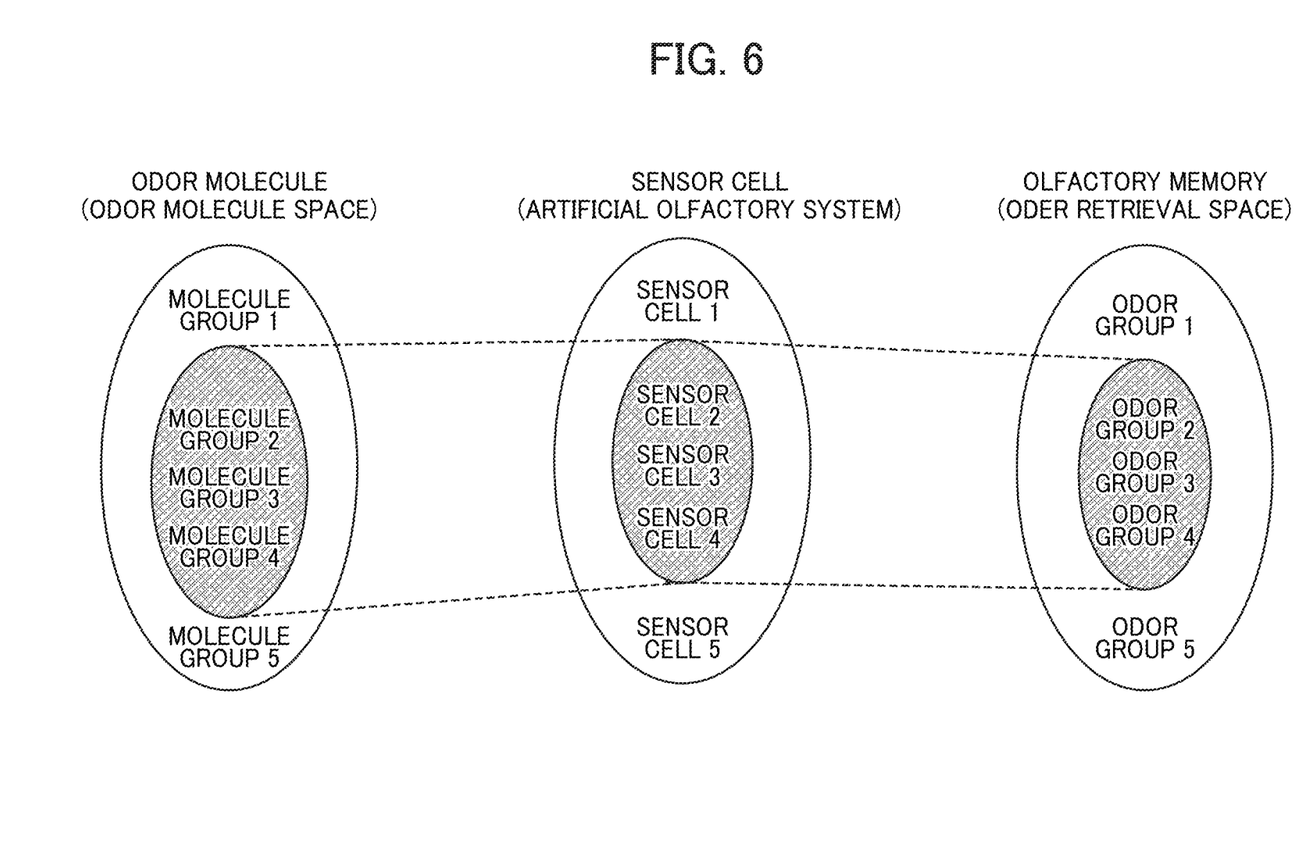
FIG. 6 is a conceptual diagram showing that five kinds of odor groups (memories) are respectively corresponding to five kinds of odor molecule groups via five kinds of sensor cell groups.

FIG. 6 is a conceptual diagram showing that five kinds of odor groups (memories) are respectively corresponding to five kinds of odor molecule groups via five kinds of sensor cell groups.

In this case, it will be assumed that the fact that the five kinds of odor groups (memories) respectively corresponds to the five kinds of odor molecule groups via the five kinds of sensor cell groups as shown in FIG. 6 has been known in advance through preliminary measurement (learning). Therefore, in the case where odor molecule groups on which an odor retrieval is performed are limited to three types, that is, the molecule groups 2 to 4 as shown in FIG. 6, by limiting signals, which are converted into electric signals and then used for retrieval processing, to signals corresponding to the sensor cells 2, 3, and 4 among five kinds of sensor cells possessed by the artificial olfactory sensing system, it becomes possible to save time and energy necessary for retrieval that is associated with signal processing performed on the sensor cells 1 and 4 that are lie outside the retrieval area.

The above is a saving method of information processing time and energy that cannot be performed by the nerve system of an organism in which signal processing moves in only one direction from an input side to an output side, that is, from an olfactory cell to an olfactory bulb and the brain cortex, and this method is a superior feature of an artificial olfactory sensing system including a million (=1,000×1,000) sensor cells of various kinds which are comparable with the sensor cells.

LIST OF REFERENCE SIGNS

11: Scanning Wiring,
12: Signal Wiring,
13: Sensor Section,
14: Sensor Cell,
15: Scanning Circuit,
16: Signal Circuit,
17: Memory Calculation Circuit (Odor Signal Addition Unit),
18: Odor Identification Unit,
21: ISFET (Ion-sensitive Transistor),
22: Well,
23: Gate Electrode of ISFET,
24: Drain Electrode of ISFET,
25: Source Electrode of ISFET,
26: Insulating Material,
27: Semiconductor,
28: Contact Electrode,
29: Olfactory Receptor,
210: Physiological Aqueous Solution,
211: Ca Ion,
212: Odor Molecule,
213: Lipid Membrane

The invention claimed is:

1. An artificial olfactory sensing system comprising:
a plurality of sensor cells on a lipid membrane of each of which olfactory receptors have developed; and
a plurality of ion-sensitive field-effect transistors (ISFETs) that correspondingly exist to the sensor cells on a one-on-one basis,
wherein each response signal corresponding to each of the sensor cells showing that each of the olfactory receptors has recognized an odor molecule is converted into an electric signal by an ISFET corresponding to said each of the sensor cells.

2. The artificial olfactory sensing system according to claim 1, wherein the sensor cells are classified into a plurality of kinds, and electric signals obtained through the conversions executed by ISFETs corresponding to the same kind of sensor cells are added up.

3. The artificial olfactory sensing system according to claim 1,
wherein the plurality of ISFETs are disposed in a two-dimensional array arrangement, and
each of the plurality of ISFETs includes septums that electrically insulate a sensor cell assigned to itself from adjacent ISFETs.

4. The artificial olfactory sensing system according to claim 1, wherein ISFETs, to which the same kind of sensor cells are assigned, are specified by measuring the intensities of the output signals of ISFETs in response to a predefined odor molecule.

5. The artificial olfactory sensing system according to claim 4, wherein the intensities of the output signals of ISFETs to which the same kind of sensor cells are assigned are normalized on the basis of the average value of the intensities of the output signals of the ISFETs during a predefined time in response to a predefined odor molecule.

6. The artificial olfactory sensing system according to claim 4, wherein the output signals of ISFETs to which the same kind of sensor cells are assigned are selectively added up among the output signals of ISFETs in response to a predefined odor molecule.

7. The artificial olfactory sensing system according to claim 3, further comprising scanning wirings and signal wirings,
wherein the ISFETs included in the two-dimensional matrix-type ISFET array are disposed at the cross-points of the scanning wirings and signal wirings, and
the same kind of sensor cells are assigned to ISFETs connected to a common scanning wiring.

8. The artificial olfactory sensing system according to claim 4, wherein only the output signals of ISFETs, to which sensor cells that identify an odor molecule group that is a detection target are assigned, are processed.

* * * * *